United States Patent
Kibby

(10) Patent No.: US 6,472,441 B1
(45) Date of Patent: *Oct. 29, 2002

(54) METHODS FOR OPTIMIZING FISCHER-TROPSCH SYNTHESIS OF HYDROCARBONS IN THE DISTILLATE FUEL AND/OR LUBE BASE OIL RANGES

(75) Inventor: Charles L. Kibby, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 09/624,172

(22) Filed: Jul. 24, 2000

(51) Int. Cl.$^7$ .................. C07C 27/00; C07C 5/22; C12Q 1/00; C10L 1/04; C10G 71/00
(52) U.S. Cl. ............... 518/715; 518/700; 585/671; 435/4; 208/15; 208/18
(58) Field of Search ............... 518/700, 715; 585/671; 435/4; 208/15, 18

(56) References Cited

U.S. PATENT DOCUMENTS

| | | | |
|---|---|---|---|
| 2,662,090 A | 12/1953 | Scharmann | 260/449.6 |
| 2,686,195 A | 8/1954 | McAdams et al. | 260/449.6 |
| 2,735,862 A | 2/1956 | Buchmann et al. | 260/449.6 |
| 2,850,515 A | 9/1958 | Riblett et al. | 260/449.6 |
| 2,882,244 A | 4/1959 | Milton | 252/455 |
| 3,130,007 A | 4/1964 | Breck | 23/113 |
| 3,216,789 A | 11/1965 | Breck | 23/113 |
| 3,484,499 A | 12/1969 | Lester et al. | 260/673 |
| 3,546,102 A | 12/1970 | Bertolacini | 208/138 |
| 3,574,092 A | 4/1971 | Mitsche | 208/139 |
| 3,668,268 A | 6/1972 | Mulaskey | 260/676 |
| 3,668,269 A | 6/1972 | Chloupek | 260/676 R |
| 3,679,575 A | 7/1972 | Bertolacini | 208/65 |
| 3,692,470 A | 9/1972 | Ciric | 423/328 |
| 3,699,035 A | 10/1972 | Hughes et al. | 208/92 |
| 3,702,886 A | 11/1972 | Argauer et al. | 423/328 |
| 3,709,979 A | 1/1973 | Chu | 423/328 |
| 3,728,410 A | 4/1973 | Hughes | 260/668 B |
| 3,773,845 A | 11/1973 | Hughes | 260/676 R |
| 3,775,505 A | 11/1973 | Hughes | 260/676 |
| 3,784,622 A | 1/1974 | Hughes | 260/676 R |
| 3,808,285 A | 4/1974 | Hughes | 260/676 R |
| 3,832,449 A | 8/1974 | Rosinski et al. | 42/328 |
| 3,856,876 A | 12/1974 | Burnett | 260/676 R |
| RE28,341 E | 2/1975 | Wadlinger et al. | 208/120 |
| 3,864,417 A | 2/1975 | Hughes | 260/676 R |
| 3,914,330 A | 10/1975 | Hughes | 260/676 R |
| 3,953,537 A | 4/1976 | Chloupek et al. | 260/676 R |
| 3,972,983 A | 8/1976 | Ciric | 423/328 |
| 4,016,245 A | 4/1977 | Plank et al. | 423/328 |
| 4,018,711 A | 4/1977 | Bertolacini | 252/455 Z |
| 4,039,302 A | 8/1977 | Khera | 48/197 |
| 4,042,614 A | 8/1977 | Vannice et al. | 260/449 |
| 4,076,842 A | 2/1978 | Plank et al. | 423/328 |
| 4,077,995 A | 3/1978 | Khera | 260/449.6 |
| 4,086,262 A | 4/1978 | Chang | 260/449.6 |
| 4,088,671 A | 5/1978 | Kobylinski | 260/449.6 |
| 4,104,320 A | 8/1978 | Bernard et al. | 260/673.5 |
| RE29,948 E | 3/1979 | Dwyer | 208/110 |
| 4,151,190 A | 4/1979 | Murchison et al. | 260/449 R |
| 4,171,320 A | 10/1979 | Vannice et al. | 260/449 R |
| 4,206,134 A | 6/1980 | Kugler et al. | 260/449 R |
| 4,241,036 A | 12/1980 | Flanigen et al. | 423/328 |
| 4,294,725 A | 10/1981 | Fraenkel et al. | 252/455 Z |
| 4,347,121 A | 8/1982 | Mayer et al. | 208/58 |
| 4,347,394 A | 8/1982 | Detz et al. | 585/419 |
| 4,370,224 A | 1/1983 | Eberly, Jr. et al. | 208/139 |
| 4,417,083 A | 11/1983 | Bernard et al. | 585/419 |

(List continued on next page.)

FOREIGN PATENT DOCUMENTS

| | | |
|---|---|---|
| EP | 353915 | 7/1989 |
| GB | 1117568 | 11/1966 |
| GB | 2050859 A | 5/1980 |
| WO | WO98/38147 A1 | 9/1998 |

OTHER PUBLICATIONS

Amelse, J.A., et al., "Iron Alloy Fischer–Tropsch Catalysts; III. Conversion Dependence of Selectivity and Water–Gas Shift," *J. Catalysis*, No. 72(1):95–110 (1981).

Bianchi et al., "Fischer–Tropsch synthesis on Co and Co(Ru–doped) ETS–10 titanium silicate catalysts," *Catalysis Lett.*, 41(1–2):79–82 (1996).

Courty, P., and Delmon, B., "Chimie Minérale.—Obtention d'oxydes mixtes divisés par décomposition de précurseurs amorphes (sels organiques amorphes)," *C.R. Acad. Sc. Paris*, p. 268 (May 28, 1969).

(List continued on next page.)

Primary Examiner—Jafar Parsa
(74) Attorney, Agent, or Firm—Burns, Doane, Swecker & Mathis, L.L.P.

(57) ABSTRACT

Methods for converting of syngas to higher molecular weight products using Fischer-Tropsch synthesis, and methods for optimizing the catalyst systems in the synthesis, are disclosed. In one embodiment, the methods use cobalt/ruthenium Fischer-Tropsch catalysts in combination with an olefin isomerization catalyst, which isomerizes double bonds in $C_4+$ olefins as they are formed. In another embodiment, the methods use Fischer-Tropsch catalysts that may or may not be cobalt/ruthenium catalysts, in combination with olefin isomerization catalysts which are acidic enough to isomerize the $C_4+$ olefins but not too acidic to cause rapid coking. A benefit of using the relatively less acidic zeolites is that the ratio of iso-paraffins to aromatics is increased relative to when more acidic zeolites are used. Also, the relatively less acidic zeolites do not coke as readily as the relatively more acidic zeolites. The methods can advantageously be optimized using combinatorial chemistry, in which a database of combinations of catalyst systems and, optionally, reaction conditions, which provide various product streams, are generated. As market conditions vary and/or product requirements change, conditions suitable for forming desired products can be identified with little or no downtime.

14 Claims, 1 Drawing Sheet

U.S. PATENT DOCUMENTS

| | | | |
|---|---|---|---|
| 4,434,311 A | 2/1984 | Buss et al. | 585/444 |
| 4,447,316 A | 5/1984 | Buss et al. | 208/138 |
| 4,507,517 A | 3/1985 | Devries et al. | 585/415 |
| 4,534,853 A | 8/1985 | Long et al. | 208/120 |
| 4,544,674 A | 10/1985 | Fiato et al. | 518/717 |
| 4,552,731 A | 11/1985 | Vaughan | 423/118 |
| 4,556,477 A | 12/1985 | Dwyer | 208/111 |
| 4,579,986 A | 4/1986 | Sie | 585/324 |
| 4,585,747 A | 4/1986 | Valyocsik | 502/62 |
| 4,599,474 A | 7/1986 | Devries et al. | 585/415 |
| 4,624,968 A | 11/1986 | Kim et al. | 518/707 |
| 4,676,885 A | 6/1987 | Bush | 208/49 |
| 4,704,487 A | 11/1987 | Devries et al. | 484/417 |
| 4,704,493 A | 11/1987 | Devries et al. | 585/415 |
| 4,709,108 A | 11/1987 | Devries et al. | 585/415 |
| 4,734,537 A | 3/1988 | Devries et al. | 585/415 |
| 4,810,357 A | 3/1989 | Chester et al. | 208/78 |
| 4,814,533 A | 3/1989 | Devries et al. | 585/407 |
| 4,814,534 A | 3/1989 | Devries et al. | 585/407 |
| 4,814,538 A | 3/1989 | Devries et al. | 585/500 |
| 4,826,667 A | 5/1989 | Zones et al. | 423/277 |
| 4,834,958 A | 5/1989 | Zones | 423/277 |
| 4,859,442 A | 8/1989 | Zones et al. | 423/277 |
| 4,910,006 A | 3/1990 | Zones | 423/328 |
| 4,963,337 A | 10/1990 | Zones | 423/277 |
| 5,053,373 A | 10/1991 | Zones | 502/64 |
| 5,104,902 A | 4/1992 | Bessell | |
| 5,106,801 A | 4/1992 | Zones | 502/64 |
| 5,107,047 A | 4/1992 | Del Rossi et al. | 585/666 |
| 5,162,284 A | 11/1992 | Soled | 502/324 |
| 5,177,281 A | 1/1993 | Haag | 585/324 |
| 5,200,377 A | 4/1993 | Zones et al. | 502/62 |
| 5,202,014 A | 4/1993 | Zones et al. | 208/46 |
| 5,237,121 A | 8/1993 | Rahmim et al. | 585/671 |
| 5,254,514 A | 10/1993 | Nakagawa | 502/62 |
| 5,316,753 A | 5/1994 | Nakagawa | 423/706 |
| 5,348,982 A | 9/1994 | Herbolzheimer et al. | 518/700 |
| 5,437,855 A | 8/1995 | Valyocsik | 423/706 |
| 5,463,161 A | 10/1995 | Gajda et al. | 585/671 |
| 5,523,511 A | 6/1996 | Helsig et al. | 585/671 |
| 5,559,068 A | 9/1996 | Chen et al. | 502/213 |
| 5,580,540 A | 12/1996 | Nakagawa | 423/718 |
| 5,591,421 A | 1/1997 | Zones et al. | 423/706 |
| 5,624,657 A | 4/1997 | Vaughan | 423/700 |
| 5,648,585 A | 7/1997 | Murray et al. | 585/671 |
| 5,689,031 A * | 11/1997 | Berlowitz et al. | 585/734 |
| 5,756,419 A | 5/1998 | Chaumette et al. | 502/313 |
| 5,840,485 A * | 11/1998 | Lebl et al. | 435/6 |
| 5,849,975 A | 12/1998 | Kluksdahl et al. | 585/671 |
| 5,856,365 A | 1/1999 | Zones et al. | 518/715 |
| 5,939,350 A | 8/1999 | Singleton et al. | 502/230 |
| 5,965,783 A | 10/1999 | Gee et al. | 585/664 |
| 5,980,839 A | 11/1999 | Bier et al. | 422/209 |
| 6,001,311 A | 12/1999 | Brennan | 422/131 |
| 6,004,617 A * | 12/1999 | Schultz et al. | 427/8 |
| 6,030,917 A | 2/2000 | Weinberg et al. | 502/104 |
| 6,036,923 A | 3/2000 | Laugharn, Jr. et al. | 422/82.13 |
| 6,054,415 A | 4/2000 | Gee et al. | 507/103 |

OTHER PUBLICATIONS

Deckwer, W.–D., et al., "Modeling the Fischer–Tropsch Synthesis in the Slurry Phase," *Ing. Eng. Chem. Process Des. Dev.*, 21(2):231–241 (1982).

*Gmelins Handbuch der Anorganische Chemie 8*, Auflage (1959), p. 59.*

Hu, Y.C., "Unconventional olefin processes,", *Hydrocarbon Processing*, May 1983, 88–96.

Jothimurugesan and Ganwal, "Titania–Supported Bimetallic Catalysts Combined with AZSM–5 for Fischer–tropsch Synthesis," *Ind. and Eng. Chemistry Res.*, 37(4):1181–1188 (1998).

Khan, M.K.Z., et al., *AIChE 1981 Summer Nat'l Meeting Preprint No. 408*, "The Synthesis of Light Hydrocarbons from CO and $H_2$ Mixtures over Selected Metal Catalysts", ACS $173^{rd}$ Symposium, Fuel Division, New Orleans (Mar. 1977).

Kitzelmann, D., et al., "Zur selektiven Hydrierung von Kohlenmonoxid zu $C_2$–bis $C_4$–Olefinen," *Chem. Ing. Tech.*, 49(6):463–468 (1977).

Kölbel et al., "The Fischer–Tropsch Synthesis in the Liquid Phase," *Catal. Rev.–Sci. Eng.*, 21(n):225–274 (1980).

Lo, C., et al., "Mössbauer and Magnetic Studies of Bifunctional Medium–Pore Zeolite–Iron Catalysts Used in Synthesis Gas Conversion," *Adv. Chem. Ser.*, 194:573–88 (1981).

Nakamura, M., et al., "Fischer–Tropsch Synthesis with Iron–Cobalt Alloy Catalysts," *Stud. Surf. Sci. Catal.*, 7(pt.A):432–446 (1981).

Ramachandran et al., *Bubble Column Slurry Reactor*, "Three–Phase Catalytic Reactors,", 10:308–332, Gordon and Broch Science Pub. (1983).

Shah, Y.T., et al., "Design Parameters Estimations for Bubble Column Reactors," *AIChE Journal*, 28(3):353–379 (May 1982).

Stanfield, R.M., et al., "Mössbauer Spectroscopy of Supported Fe–Co Alloy Catalysts for Fischer–Tropsch Synthesis," *J. Catalysis*, No. 72(1):37–50 (1981).

Van der Woude, F., et al., "Mössbauer Effect in Iron and Dilute Iron Alloys," *Physics Reports (Section C of Physics Letters)*, 12(5):335–374 (1974).

Xu et al., "Don't rule out iron catalysts for Fischer–Tropsch synthesis," *Chemtech*, Jan. 1998, pp. 47–53.

* cited by examiner

METHODS FOR OPTIMIZING FISCHER-TROPSCH SYNTHESIS OF HYDROCARBONS IN THE DISTILLATE FUEL AND/OR LUBE BASE OIL RANGES

FIELD OF THE INVENTION

This invention is generally in the area of the combinatorial chemistry, in particular, the use of combinatorial chemistry to optimize the Fischer-Tropsch synthesis of hydrocarbons in the distillate fuel and/or lube base oil ranges.

BACKGROUND OF THE INVENTION

The majority of fuel today is derived from crude oil. Crude oil is in limited supply, and fuel derived from crude oil tends to include nitrogen-containing compounds and sulfur-containing compounds, which are believed to cause environmental problems such as acid rain.

Although natural gas includes some nitrogen- and sulfur-containing compounds, methane can be readily isolated in relatively pure form from natural gas using known techniques. Many processes have been developed which can produce fuel compositions from methane. Most of these process involve the initial conversion of methane to synthesis gas ("syngas").

Fischer-Tropsch chemistry is typically used to convert the syngas to a product stream that includes combustible fuel, among other products. A limitation associated with Fischer-Tropsch chemistry is that it tends to produce a broad spectrum of products, ranging from methane to wax. Product slates for syngas conversion over Fischer-Tropsch catalysts (Fe, Co and Ru) are controlled by polymerization kinetics with fairly constant chain growth probabilities, which fix the possible product distributions. Heavy products with a relatively high selectivity for wax are produced when chain growth probabilities are high. Methane is produced with high selectivity when chain growth probabilities are low.

Methane can be recirculated to ultimately yield combustible liquid fuel. Wax can be processed, for example, by hydrocracking and/or hydrotreating followed by oligomerization, to yield combustible liquid fuel. However, it would be advantageous to have new methods for providing a product stream from a Fischer-Tropsch process that has a higher proportion of combustible liquid fuel with less methane to recirculate and/or less wax to process.

Traditional Fischer-Tropsch synthesis has been modified by incorporating an acidic component, such as a relatively acidic zeolite, into the catalyst bed. When $C_4+$ alpha-olefins are produced, the alpha-olefins isomerize to more substituted olefins in the presence of the acid catalyst and/or form aromatics. This reduces the chain growth probability for $C_4+$ and largely minimizes wax formation. For example, U.S. Pat. No. 4,086,262 to Chang et al. teaches conducting Fischer-Tropsch synthesis with ZSM-5 intimately mixed with the Fischer-Tropsch catalyst. Chang focused on obtaining high octane gasoline (i.e., highly branched hydrocarbons in the gasoline range).

Most work since then has focused on improving the catalyst components and continues to provide highly branched hydrocarbons in the high octane gasoline range. The catalysts are typically iron catalysts, since they operate at higher temperatures where the zeolites tend to be more active. In addition to intimate mixtures of zeolites and Fischer-Tropsch catalysts, some carbon monoxide hydrogenation components have been incorporated directly on zeolites (see, for example, U.S. Pat. No. 4,294,725).

There is a growing interest in developing "greener" diesel fuels, i.e., fuels that do not contain aromatic, nitrogen or sulfur compounds. Straight chain or slightly branched paraffins in the diesel fuel range tend to have relatively high cetane values. Ideally, such fuels could be provided directly from Fischer-Tropsch reactors, if the right combinations of Fischer-Tropsch catalysts and zeolites could be found. However, known combinations of zeolites and Fischer-Tropsch catalysts to date have provided mainly highly branched paraffins in the gasoline range.

It would be advantageous to provide new catalysts compositions for converting syngas to higher molecular weight products, for example hydrocarbons in the distillate fuel and/or lube base stock base oil ranges. The present invention provides such compositions.

SUMMARY OF THE INVENTION

The present invention is directed to methods for converting syngas to hydrocarbons in the distillate fuel and/or lube base oil ranges via Fischer-Tropsch synthesis. In one embodiment, the methods use cobalt/ruthenium Fischer-Tropsch catalysts in combination with an olefin isomerization catalyst, for example a relatively acidic zeolite, for isomerizing double bonds in $C_4+$ olefins as they are formed. The composite catalysts described herein permit the Fischer-Tropsch synthesis to operate with relatively high chain growth probabilities through about $C_3$, and with relatively low chain growth probabilities above $C_4$.

In another embodiment, the methods use Fischer-Tropsch catalysts that may or may not be cobalt/ruthenium catalysts, in combination with catalysts that are acidic enough to isomerize the double bonds in $C_4+$ olefins, yet not so strongly acidic that they coke rapidly. Preferably, the catalysts are zeolites with silica/alumina ratios of between 3 and 100. An additional benefit of using the relatively less acidic zeolites is that the ratio of iso-paraffins to aromatics may be increased relative to when more acidic zeolites are used.

The methods can advantageously be optimized using combinatorial chemistry, in which a database of combinations of catalyst systems and, optionally, catalyst pretreatments and/or reaction conditions, which provide various product streams, are generated. As market conditions vary and/or product requirements change, conditions suitable for forming desired products can be identified with little or no downtime.

In this embodiment, libraries of catalysts suitable for use in a first catalyst system (Fischer-Tropsch catalysts) and a second catalyst system (olefin isomerization catalysts) are prepared. The libraries can optionally include catalysts that possess both types of activity, namely, that can convert syngas to olefins and also that isomerize the olefins.

The catalysts are preferably combined in a logical manner, for example in an A×B array, where each position in the A column includes one or more catalysts from the first catalyst system, and each position in the B row includes one or more catalysts from the second catalyst system. In this manner, virtually every possible combination of catalysts in the libraries can be evaluated. The combinations of catalysts can be evaluated using varied reaction conditions, which can provide a) a combinatorial library of product streams and a database including the combination of catalysts and reaction conditions to provide each product stream and/or b) the optimum combination of catalysts and reaction conditions for obtaining a desired product stream.

The products include olefins such as ethylene, normal paraffins, iso-paraffins, and combinations thereof, and preferably include iso-paraffins in the distillate fuel and/or lube base stock ranges, and, more preferably, iso-paraffins in the jet or diesel range.

DETAILED DESCRIPTION OF THE INVENTION

Figure 1:
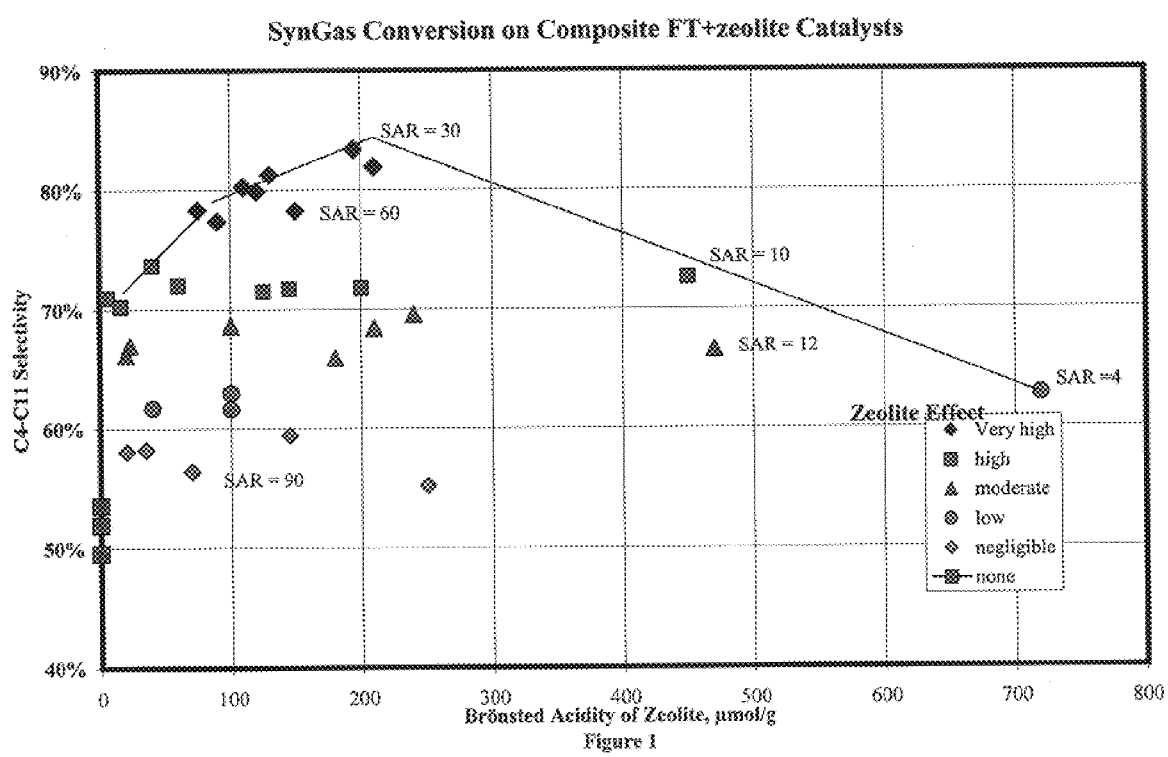
FIG. 1 is a graph showing the syngas conversion ($C_{4-11}$ selectivity) versus Bronsted acidity of the zeolite catalyst ($\mu$mol/g) using composite Fischer-Tropsch/zeolite catalysts, as described in Example 1. Black diamonds represent very high zeolite effect. Grey squares represent high zeolite effect. Grey triangles represent a moderate zeolite effect. Grey circles represent a low zeolite effect. Grey diamonds represent a negligible zeolite effect, and grey squares with lines throughout represent no zeolite effect.

The present invention is directed to methods for optimizing the conversion of syngas to hydrocarbons in the distillate fuel and/or lube base oil ranges via Fischer-Tropsch synthesis. In one embodiment, the methods use cobalt/ruthenium Fischer-Tropsch catalysts in combination with an olefin isomerization catalyst, for example a molecular sieve, for isomerizing double bonds in $C_4$+ olefins as they are formed. The composite catalysts described herein permit the Fischer-Tropsch synthesis to operate with relatively high chain growth probabilities through about $C_3$, and with relatively low chain growth probabilities above $C_4$. In another embodiment, the methods use Fischer-Tropsch catalysts that may or may not be cobalt/ruthenium catalysts, in combination with catalysts that are acidic enough to isomerize the double bonds in $C_4$+ olefins yet not so strongly acidic that they coke rapidly. Generally, the catalysts are zeolites with silica/alumina ratios of between 3 and 100. An additional benefit of using the relatively less acidic zeolites is that the ratio of iso-paraffins to aromatics may be increased relative to when more acidic zeolites are used. The synthesis can be optimized using combinatorial chemistry.

I. Fischer-Tropsch Synthesis

Fischer-Tropsch synthesis typically involves the conversion of syngas to higher molecular weight products, including olefins and paraffins. In one embodiment, the traditional Fischer-Tropsch synthesis is modified by using cobalt/ruthenium catalysts in combination with olefin isomerization catalysts.

An advantage of using cobalt/ruthenium catalysts is that they are readily activated to give metal dispersions 50 to 100% greater than over comparably loaded cobalt catalysts. This can be of particular importance when the catalysts are diluted with an isomerization catalyst, since the loss in Fischer-Tropsch activity is more tolerable.

A benefit of using the cobalt/ruthenium catalysts in combination with the olefin isomerization catalysts is that a relatively high chain growth probability for $C_1$–$C_3$ chains puts most of the product into the $C_{4+}$ range with minimum methane formation. At the same time, a relatively low chain growth probability for $C_1$–$C_3$ chains minimizes wax formation. The resulting product stream has a relatively higher yield of $C_{5-20}$ hydrocarbons than would be observed using a Fischer-Tropsch catalyst operated with constant, low chain growth probability (which tends to form relatively large amounts of methane) or operated with a constant, high chain growth probability (which tends to form relatively large amounts of wax). Further, the liquid hydrocarbons tend to have sufficient branching for them to have commercially useful pour points and viscosities.

In another embodiment, the Fischer-Tropsch/olefin isomerization catalyst combinations are optimized by using olefin isomerization catalysts that have sufficient acidity to isomerize the olefins, but not enough acidity to rapidly coke the catalyst beds. The relatively low level of acidity also results in less aromatic formation, yielding more branched hydrocarbons. This is advantageous when the desired fuel has a low aromatics specification.

The Fischer-Tropsch reaction is discussed in more detail below.

Syngas

Typically, synthesis gas contains hydrogen and carbon monoxide, and may include minor amounts of carbon dioxide and/or water. When iron-containing catalysts are used, the ratio of hydrogen/carbon monoxide is preferably between about 0.5 and 1.0, preferably around 0.5. When cobalt-containing catalysts are used (for example, cobalt/ruthenium catalysts), the ratio of hydrogen/carbon monoxide is preferably greater than 1.0, more preferably between about 1.0 and 2.0, still more preferably between about 1.0 and 1.5. A hydrogen/carbon monoxide ratio of 1.0 or less results in the formation of a relatively large proportion of oxygenated products and, for this reason, should be avoided.

The presence of sulfur, nitrogen, halogen, selenium, phosphorus and arsenic contaminants in the syngas is undesirable. For this reason, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art.

Catalysts

A. Fischer-Tropsch Catalysts

In general, Fischer-Tropsch catalysts contain a Group VIII transition metal on a metal oxide support. The catalysts may also contain a noble metal promoter(s) and/or crystalline molecular sieves. Certain catalysts are known to provide chain growth probabilities that are relatively low to moderate, and the product of the reaction includes a relatively high proportion of low molecular ($C_{2-8}$) weight olefins and a relatively low proportion of high molecular weight ($C_{30}$+) waxes. Certain other catalysts are known to provide relatively high chain growth probabilities. Such catalysts are well known to those of skill in the art and can be readily obtained and/or prepared.

Catalysts Operated with Low Chain Growth Probabilities

Typically, catalysts operated with an alpha value between about 0.600 and 0.700 are considered to have low chain growth probabilities. Catalysts operated with an alpha value between about 0.700 and 0.800 are considered to have moderate chain growth probabilities. Catalysts operated with an alpha value greater than about 0.800 are considered to have high chain growth probabilities. Catalysts can be operated with low chain growth probabilities, but that is not preferred in the methods described herein.

Typically, catalysts operated with low chain growth probabilities are low-alkalinity, iron-containing catalysts. Iron itself can be used and, when iron oxides are formed, can be reduced with hydrogen back to iron. However, because the presence of iron fines in the product stream is not preferred, and because iron oxides (rust) decrease the surface area of the catalyst available for reaction, other iron-containing catalysts have been developed. Examples of suitable iron-containing catalysts include those described in U.S. Pat. No. 4,544,674 to Fiato et al. and Xu et al., pp. 47–53, *Chemtech* (January 1998).

The iron-containing catalysts typically include at least about 10 to about 60 weight percent iron. These catalysts can be unsupported, or promoted with a refractory metal oxide ($SiO_2$, $Al_2O_3$, etc.), alkali (K, Na, Rb) and/or Group IB metals (Cu, Ag).

Co-precipitated iron-based catalysts, including those containing cobalt, can be used. High levels of cobalt in an iron-cobalt alloy are known to produce enhanced selectivity to olefinic products, as described, for example, in *Stud. Surf. Sci. Catal.* 7, Pt/A, p. 432 (1981).

Examples of co-precipitated iron-cobalt catalysts and/or alloys include those described in U.S. Pat. Nos. 2,850,515, 2,686,195, 2,662,090, and 2,735,862; *AICHE* 1981 *Summer Nat'l Meeting Preprint No.* 408, "The Synthesis of Light Hydrocarbons from CO and $H_2$ Mixtures over Selected Metal Catalysts" ACS 173rd Symposium, Fuel Division, New Orleans, March 1977; *J. Catalysis* 1981, No. 72(1), pp. 37–50; *Adv. Chem. Ser.* 1981, 194, 573–88; *Physics Reports (Section C of Physics Letters)* 12 No. 5 (1974) pp. 335–374; UK patent application No. 2050859A; *J. Catalysis* 72, 95–110 (1981); Gmelins Handbuch der Anorganische Chemie 8, Auflage (1959), pg. 59; *Hydrocarbon Processing*, May 1983, pp. 88–96; and *Chem. Ing. Tech.* 49 (1977) No. 6, pp. 463–468.

Methods for producing high surface area metal oxides are described, for example, in the French article, *C. R. Acad. Sc. Paris*, p. 268 (May 28, 1969) by P. Courte and B. Delmon. Metal oxides with a high surface area are prepared by evaporating to dryness aqueous solutions of the corresponding glycolic acid, lactic acid, malic or tartaric acid metal salts. One oxide that was prepared was $CoFe_2O_4$.

Iron-cobalt spinels which contain low levels of cobalt, in an iron/cobalt atomic ratio of 7:1 to 35:1, are converted to Fischer-Tropsch catalysts upon reduction and carbiding (see, for example, U.S. Pat. No. 4,544,674 to Fiato et al.). These catalysts tend to exhibit high activity and selectivity for $C_2$–$C_6$ olefins and low methane production.

The contents of each of the patents and publications referred to above is hereby incorporated by reference.

Catalysts Operated With High Chain Growth Probabilities

Typically, catalysts operated with high chain growth probabilities contain cobalt, ruthenium, or iron promoted heavily with alkali.

One suitable cobalt catalyst that can be used is described in U.S. Pat. No. 4,579,986, as satisfying the relationship:

$$(3+4R)>L/S>(0.3+0.4R),$$

wherein:
  L=the total quantity of cobalt present on the catalyst, expressed as mg Co/ml catalyst;
  S=the surface area of the catalyst, expressed as $m^2$/ml catalyst; and
  R=the weight ratio of the quantity of cobalt deposited on the catalyst by kneading to the total quantity of cobalt present on the catalyst.

Other suitable catalysts include those described in U.S. Pat. Nos. 4,077,995, 4,039,302, 4,151,190, 4,088,671, 4,042,614 and 4,171,320. U.S. Pat. No. 4,077,995 discloses a catalyst that includes a sulfided mixture of CoO, $Al_2O_3$ and ZnO. U.S. Pat. No. 4,039,302 discloses a mixture of the oxides of Co, Al, Zn and Mo. U.S. Pat. No. 4,151,190 discloses a metal oxide or sulfide of Mo, W, Re, Ru, Ni or Pt, plus an alkali or alkaline earth metal, with Mo—K on carbon being preferred.

Cobalt/Ruthenium Catalysts

In a preferred embodiment, cobalt/ruthenium catalysts are used. These catalysts have very high activities due to easy activation at low temperatures.

Fischer-Tropsch catalysts including cobalt and ruthenium are known to those of skill in the art. For example, U.S. Pat. No. 4,088,671 discloses incorporating a small amount of ruthenium on a cobalt catalyst. Supported ruthenium catalysts are also disclosed, for example, in U.S. Pat. Nos. 4,042,614 and 4,171,320. Titania-supported cobalt/ ruthenium catalysts are described in Jothimurugesan and Ganwal, *Ind. and Eng. Chemistry Res.*, 37(4): 1181–1188 (1998) and Bianchi et al., *Catalysis Lett.*, 41(1–2):79–82 (1996).

Cobalt/ruthenium catalysts are also described in U.S. Pat. Nos. 5,756,419 and 5,939,350. U.S. Pat. No. 5,939,350 discloses a process for preparing a supported, ruthenium-promoted, cobalt catalyst. The process involves calcining a support having a porous structure, co-impregnating the support with an aqueous solution including cobalt nitrate and a water-soluble ruthenium compound to obtain a catalyst precursor, then drying, calcining and reducing the catalyst precursor.

U.S. Pat. No. 5,856,365 discloses a process for preparing a Fischer-Tropsch catalyst that includes an inert support, cobalt, ruthenium and either scandium or yttrium. The method involves preparing a first catalytic precursor (A) containing cobalt and the inert support. The precursor is subsequently calcined, reduced and passivated. Ruthenium is then deposited on the first catalytic support (A). The resulting catalyst is subsequently calcined, reduced and passivated. Scandium or yttrium is then deposited on the catalytic precursor (B), and the catalyst is subsequently calcined, reduced and passivated.

Cobalt and ruthenium can also be deposited on a zeolite catalyst, to provide a single catalyst with Fischer-Tropsch and olefin-isomerization activity. Methods for depositing metals on zeolites are well known to those of skill in the art, and are described, for example, in U.S. Pat. No. 4,294,725.

Any of the catalysts described in these references above can be used. The contents of each of these references is hereby incorporated by reference.

Catalyst Supports

The type of catalyst support can influence methane production. Suitable metal oxide supports or matrices which can be used to minimize methane production include alumina, titania, silica, magnesium oxide, alkaline earth titanates, alkali titanates, rare earth titanates and mixtures thereof. The catalysts can include any or all of these supports, in varying ratios of weight of support to weight of catalyst.

Typically, the individual catalyst components have a particle size of between 10 and 110 microns, preferably between 20 and 80 microns, more preferably between 25 and 65 microns, and have a density of between 0.25 and 0.9 g/cc, preferably between 0.3 and 0.75 g/cc. The components can be combined, added to a binder, and formed into larger catalyst shapes, for example, by pelleting, extrusion and the like.

The catalysts typically include one or more of the above-mentioned catalytic metals on one of the above-mentioned catalyst supports.

Promoters and Noble Metals

Methane selectivity is also influenced by the choice of promoter. Alkali metal promoters are known for reducing the methane selectivities of iron catalysts. Noble metals and other metals such as ruthenium, supported on inorganic refractory oxide supports, exhibit superior hydrocarbon synthesis characteristics with relatively low methane production. Where a noble metal is used, platinum and palladium are generally preferred. However, ruthenium is preferred over platinum or palladium because it has much stronger Fischer-Tropsch activity than either platinum or palladium. Accordingly, alkali metal promoters and/or noble metals can be included with the catalysts.

Manganese Salts

The tendency for olefins to be readily hydrogenated on cobalt-containing catalysts tends to minimize the overall yield of $C_5+$ products. The presence of manganese and manganese salts in the catalyst and/or support tends to decrease the rate of olefin hydrogenation, and, for this reason, may be preferred. Examples of suitable manganese-containing materials that can be used include manganese-containing zeolites, unsupported and alumina-supported manganese oxide catalysts, manganese molybdate. Examples of manganese oxide-containing catalysts and/or supports include MnO, $Al_2O_3$—MnO, $SiO_2$—MnO, MnO-carbon, Group IVB-manganese oxides, Group VB-manganese oxides, Group IA (alkali metal)-manganese oxides, Group IIA (alkaline earth metal)-manganese oxides and rare earth-manganese oxides and mixtures thereof. The preferred support is manganese oxide. Suitable manganese-containing catalysts are described, for example, in U.S. Pat. Nos. 4,206,134 and 5,162,284. When these catalysts are used in Fischer-Tropsch chemistry under certain conditions, Cu-promoted $Co_2MnO_4$ showed an increased olefin content in the products versus Cu-promoted $Co_3O_4$. U.S. Pat. No. 4,206,134 discloses using MnO-supported Ru catalysts which also show this effect. U.S. Pat. No. 4,624,968 discloses using an iron/manganese/potassium catalyst in Fischer-Tropsch synthesis.

Catalysts in spinel form have been formed that include cobalt and manganese, in particular copper-promoted cobalt-manganese spinels with the formula $CO_{3-x}MnO_4$, where x is from about 0.5 to about 1.2, preferably from about 0.7 to about 1.0, most preferably about 1.0. The ratio of cobalt to manganese in the spinel is between about 1.5:1 and about 5:1. The amount of copper promoter in the composition is typically from about 0.1 to about 5 gram atom percent based on the total gram atoms of cobalt and manganese of the dry composition. Copper-promoted cobalt-manganese catalysts appear to be significantly more active, and also better at minimizing olefin hydrogenation, than analogs promoted with copper but not containing manganese, or catalysts containing manganese but not promoted with copper. Ruthenium-containing catalysts can be used with manganese oxide, other manganese-containing oxides or mixtures of various manganese oxides as a catalyst support.

Any and all of these catalysts can be used. The disclosures of each of the patents and articles discussed above are incorporated herein by reference in their entirety.

B. Olefin Isomerization Catalysts

Any catalyst that isomerizes alpha-olefins to internal olefins, and is compatible with the Fischer-Tropsch catalyst, can be used. Typically, relatively acidic zeolites are used to isomerize alpha olefins. Preferably, the catalyst combinations (Fischer-Tropsch catalyst and olefin isomerization catalyst) have sufficient activity and selectivity to produce high yields of paraffins and iso-paraffins in the diesel fuel or lube base stock ranges and do not readily deactivate under conditions of use. Catalysts and reaction conditions for isomerizing olefins are well known to those of skill in the art. Such catalysts and conditions are described, for example, in U.S. Pat. Nos. 5,107,047, 5,177,281, 5,237,121, 5,463,161, 5,523,511, 5,648,585, 5,849,975, 5,965,783, and 6,054,415, the contents of which are hereby incorporated by reference.

Zeolites

Catalysts useful for isomerizing alpha olefins typically include one or more zeolites and/or non-zeolitic molecular sieves. Those zeolites that are relatively acidic tend to be more efficient at olefin isomerization than those that are relatively less acidic, but also tend to provide more aromatics and/or tend to deactivate more readily.

The zeolites and/or molecular sieves are preferably large and/or intermediate pore size zeolites, although zeolites with small pore sizes can also be used. Examples of these catalysts, any and all of which can be used, are described, for example, in U.S. Pat. Nos. 3,546,102; 3,574,092; 3,679,575; 4,018,711; 4,104,320; 4,347,394; 4,370,224; 4,417,083; 4,434,311; 4,447,316 and 5,559,068. Mordenite, ZSM-type zeolites, zeolite L, Faujasites X and Y, and the zeolite omega are preferred zeolites. L-zeolites and zeolites having an L-zeolite-type channel structure and size, such as ECR-2, which is described in U.S. Pat. No. 4,552,731, and ECR-31, which is described in U.S. Pat. No. 5,624,657 (Vaughan) are also preferred zeolites.

The composition of type L-zeolite expressed in terms of mole ratios of oxides, may be represented by the following formula:

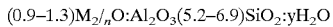

$$(0.9-1.3)M_{2/n}O:Al_2O_3(5.2-6.9)SiO_2:yH_2O$$

In the above, formula M represents a cation, n represents the valence of M, and y may be any value from 0 to about 9. Zeolite L, its X-ray diffraction pattern, its properties, and method for its preparation are described in detail in, for example, U.S. Pat. No. 3,216,789, the contents of which is hereby incorporated by reference. The actual formula may vary without changing the crystalline structure. For example, the mole ratio of silicon to aluminum (Si/Al) may vary from 1.0 to 3.5.

Examples of useful large pore zeolites include ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44 and MCM-58, any and all of which can be used. ZSM-3 is described in U.S. Pat. No. 3,415,736. ZSM-4 is described in UK Application No. 1,117,568. ZSM-10 is described in U.S. Pat. No. 3,692,470. ZSM-12 is described in U.S. Pat. No. 3,832,449. ZSM-20 is described in U.S. Pat. No. 3,972,983. Zeolite beta is described in U.S. Pat. No. Re. 28,341 (of original U.S. Pat. No. 3,308,069). Zeolite omega is described in U.S. Pat. No. 4,241,036. Zeolite L is described in U.S. Pat. No. 3,216,789. Zeolite X is described in U.S. Pat. No. 2,882,244. Zeolite Y is described in U.S. Pat. No. 3,130,007. LZ-210, LZ-210M, LZ-210-T, LZ-210-A and mixtures thereof are described in U.S. Pat. No. 4,534,853. SSZ-24 is described in U.S. Pat. No. 4,834,977. SSZ-26 is described in U.S. Pat. No. 4,910,006. SSZ-31 is described in U.S. Pat. No. 5,106,801. SSZ-33 is described in U.S. Pat. No. 4,963,337. SSZ-35 is described in U.S. Pat. No. 5,316,753. SSZ-37 is described in U.S. Pat. No. 5,254,514. SSZ-41 is described in U.S. Pat. No. 5,591,421. SSZ-42 is described in U.S. Serial No. 08/199,040. SSZ-44 is described in U.S. Pat. No. 5,580,540. MCM-58 is described in U.S. Pat. No. 5,437,855.

Examples of useful intermediate pore size zeolites include ZSM-5, ZSM-11, ZSM-22, ZSM-23, ZSM-35; ZSM-48, ZSM-57, SUZ-4, SSZ-23; SSZ-25; SSZ-28, SSZ-32, and SSZ-36. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application No. 353,915. SSZ-23 is described in U.S. Pat. No. 4,859,422. SSZ-25 is described in U.S. Pat. Nos. 4,827,667 and 5,202,014. SSZ-28 is described in U.S. Pat. No. 5,200,377. SSZ-32 is described in U.S. Pat. No. 5,053,373. The entire contents of all these patents and patent applications are incorporated herein by reference, and any and all of the catalysts described therein can be used.

The isomerization of alpha olefins is believed to involve an interaction with an acidic catalyst component. Of USY zeolites that were evaluated (in Example 1, described in detail below), those with a relatively high silica/alumina ratio (SAR) were relatively inactive. In those with relatively low SAR's, rapid deactivation is observed. Those USY zeolites with intermediate SAR's had large effects on the product distributions. It is likely that the low activity of the high SAR versions is due to their low acidity, while the high deactivation rates for USY's with low SAR is due to their very high acidity. Some catalysts develop acidity due to incorporation of other metals than aluminum, for example, magnesium, and the acidity is not due entirely to the SAR for such catalysts. Accordingly, the Brönsted acidity of the catalysts may be as important or more important than the SAR. The SAR describes both lattice aluminum and extra lattice aluminum, where only lattice aluminum gives rise to Brönsted acidity. A suitable range is between 50 and 250 $\mu$mol/g.

The entire contents of all the above-cited patents are incorporated herein by reference, and any and all of the zeolites described therein with suitable SAR's can be used.

Carriers

Any of the catalysts described above and combinations thereof, may be formed in any conventional manner, such as tableting, pelleting, or supporting the active catalyst material on a carrier. The carrier is preferably inert and may include silica, alumina, Alundum, clay, alumina-silica, silicon carbide, zeolite, and the like. The catalysts can be incorporated into solid particles in which the catalyst is present in an amount effective to promote the desired conversion.

In one aspect, the solid particles comprise a catalytically effective amount of the catalyst and at least one matrix material, preferably selected from the group consisting of binder materials, filler materials, and mixtures thereof, to provide a desired property or properties, e.g., desired catalyst dilution, mechanical strength, and the like, to the solid particles. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like. If matrix materials, e.g., binder and/or filler materials, are included in the catalyst composition, the catalysts typically comprise about 1 to 99%, more typically about 5 to about 90%, by weight of the total composition.

The preparation of solid particles comprising catalyst and matrix materials is conventional and well known in the art and, therefore, need not be discussed in detail herein.

Composite Catalysts Including Fischer-Tropsch and Olefin Isomerization Catalysts In a preferred embodiment, composite catalysts are used to provide optimum Fischer-Tropsch syntheses, with low (preferably less than about 10% based on the number of carbon atoms) methane yields and low wax yields. The cobalt/ruthenium component and the olefin isomerization component can be mixed in any suitable ratio that provides adequate carbon monoxide conversion and also adequate olefin isomerization. Preferably, the ratio of Fischer-Tropsch catalyst to olefin-isomerization catalyst is between about ½ and $19/1$ by weight.

Operating Conditions

Examples of conditions for performing Fischer-Tropsch type reactions are well known to those of skill in the art. Suitable conditions are described, for example, in U.S. Pat. Nos. 4,704,487, 4,507,517, 4,599,474, 4,704,493, 4,709,108, 4,734,537, 4,814,533, 4,814,534 and 4,814,538, the contents of each of which are hereby incorporated by reference in their entirety.

The Fischer-Tropsch reaction using iron-containing catalysts is typically conducted at temperatures between about 270° C. and 280° C., at a pressure of between about 1 and 20 ATM, in a slurry reactor or a fluidized bed reactor. Typical synthesis gas linear velocity ranges in the reactor are between about 2 and 40 cm per sec., preferably between about 6 and 10 cm per sec.

The Fischer-Tropsch reaction using cobalt-containing catalysts is typically conducted in either a fixed bed reactor or a slurry reactor, where slurry reactors are preferred. The operating temperature of the fixed bed reactor is between about 200° C. and 225° C., and the operating temperature of the slurry reactor is between about 225° C. and 250° C., with a temperature around 240° C. preferred. Typical synthesis gas linear velocity ranges in the reactor are from about 2 to 40 cm per sec., preferably from about 6 to 10 cm per sec. The pressure is preferably between about 1 and 30 ATM, with pressures between 20 and 30 ATM being particularly preferred. Above about 30 ATM, carbonyls may be formed and, therefore, pressures significantly about 30 ATM are not preferred. Further, the rate of reaction tends to increase with increased pressure, but tends to level off due to hydrodynamic problems at around 30 ATM.

The catalyst space velocities are typically between about 100 and 10,000 cc/g/h, preferably between about 300 and 3,000 cc/g/h, for either set of reaction conditions.

As discussed above, slurry reactors can be preferred for either set of conditions. Bubble column slurry reactors can be particularly preferred. Details regarding bubble column slurry reactors can be found, for example, in Y. T. Shah et al., "Design Parameters Estimations for Bubble Column Reactors," *AIChE Journal*, 28(3), pp. 353–379 (May 1982); Ramachandran et al., *Bubble Column Slurry Reactor*, "Three-Phase Catalytic Reactors," Chapter 10, pp. 308–332, Gordon and Broch Science Publishers (1983); Deckwer et al., "Modeling the Fischer-Tropsch Synthesis in the Slurry Phase," *Ind. Eng. Chem. Process Des. Dev.*, 21(2), pp. 231–241 (1982); Kölbel et al., "The Fischer-Tropsch Synthesis in the Liquid Phase," *Catal. Rev.-Sci. Eng.*, 21(n), pp. 225–274 (1980); and U.S. Pat. No. 5,348,982, the contents of each of which are hereby incorporated by reference in their entirety.

Since the catalyst metal may be present in the catalyst in the form of an oxide, the catalyst may be reduced with hydrogen prior to contact with the slurry liquid. The starting slurry liquid is typically a heavy hydrocarbon that is viscous enough to keep the catalyst particles suspended (typically a viscosity between 4 and 100 centistokes at 100° C.) and a low enough volatility to avoid vaporization during operation (typically an initial boiling point range of between about 350° C. and 550° C.). The slurry liquid is preferably essentially free of contaminants such as sulfur, phosphorous or chlorine compounds. Initially, it may be desirable to use a synthetic hydrocarbon fluid such as a synthetic olefin oligomer as the slurry fluid.

The slurry typically has a catalyst concentration of between about 2 and 40 percent catalyst, based on the total weight of the catalyst, i.e., metal plus support.

Although the stages described herein are described in terms of a Fischer-Tropsch reaction, these stages can optionally be performed using various modifications of the literal Fischer-Tropsch process where hydrogen (or water) and carbon monoxide (or carbon dioxide) are converted to hydrocarbons (e.g., paraffins, ethers, etc.). Thus, the term Fischer-Tropsch type product or process is intended to apply to Fischer-Tropsch processes and products and the various modifications thereof and the products thereof. For example, the term is intended to apply to the Kolbel-Engelhardt process. When performed commercially, the $CO_2$ product can be returned to the syngas generator and combined with methane (and some air) to form additional syngas.

The products from Fischer-Tropsch reactions generally include a gaseous reaction product and a liquid reaction product. The gaseous reaction product includes hydrocarbons boiling below about 650° F. (e.g., tail gases through middle distillates). The liquid reaction product (the condensate fraction) includes hydrocarbons boiling above about 650° F. (e.g., vacuum gas oil through heavy paraffins).

Commercially, the minus 650° F. product is typically separated into a tail gas fraction and a condensate fraction, i.e., about $C_5$ to $C_{20}$ normal paraffins and higher boiling hydrocarbons, using, for example, a high pressure and/or lower temperature vapor-liquid separator or low pressure separators or a combination of separators. The fraction boiling above about 650° F. (the condensate fraction) is typically separated into a wax fraction boiling in the range of about 650° F.–1200° F. after removing particulate catalyst fines and one or more fractions boiling above about 1200° F. The wax fraction primarily contains $C_{20}$ to $C_{50}$ linear paraffins with relatively small amounts of higher boiling branched paraffins. The separation is typically effected by fractional distillation. However, if combinatorial libraries of catalyst combinations are being evaluated, the separation is preferably effected by gas chromatography. The amounts of each component can be determined, and the information regarding the effectiveness of each set of reaction conditions can be stored.

Products

In any Fischer-Tropsch synthesis, methane and/or wax and other heavy products will invariably be produced to some degree. The major products include olefins such as ethylene, normal and iso-paraffins, and combinations thereof, preferably in the distillate fuel ranges, and, more preferably, in the jet or diesel range.

Branching may be advantageous in a number of end-uses, particularly when increased octane values and/or decreased pour points are desired. The degree of isomerization is preferably greater than 1, and more preferably, greater than 3 moles of isoparaffin per mole of n-paraffin. When used in a diesel fuel composition, the products preferably have a cetane number of at least 60.

Commercially, higher molecular weight products, for example waxes, can either be isolated and used directly, or can be reacted to form lower molecular weight products, as desired. For example, high molecular weight products can be hydrocracked to provide lower molecular weight products, increasing the yield of liquid combustible fuels. Hydrocracking refers to a catalytic process, usually carried out in the presence of free hydrogen, in which the cracking of the larger hydrocarbon molecules is a primary purpose of the operation. Catalysts used in carrying out hydrocracking operations are well known in the art, and it should not be necessary to describe them in detail here. See, for example, U.S. Pat. Nos. 4,347,121 and 4,810,357 for general descriptions of hydrotreating, hydrocracking, and typical catalysts used in each process. The product from the hydrocracking can be subject to distillation and/or catalytic isomerization to provide lube oils, diesel fuel, and the like.

Combinatorial Chemistry

The methods can be optimized using a combinatorial approach to identify combinations of catalyst systems useful for performing the Fischer-Tropsch reactions. The catalyst combinations include a first catalyst system (a Fischer-Tropsch catalyst) and a second catalyst system (an olefin isomerization catalyst). The combinations can be laid out in a logical fashion, for example in arrays. Where different classes of Fischer-Tropsch catalysts are used, for example catalysts with low chain growth probabilities and catalysts with high chain growth probabilities, they can advantageously be placed in sub-arrays, where the entire array includes all of the above catalysts. The arrays can be ordered in such a fashion as to expedite synthesis and/or evaluation, to maximize the informational content obtained from the testing and to facilitate the rapid evaluation of that data.

The reactions are preferably carried out in a reaction vessel capable of performing a plurality of simultaneous or substantially simultaneous reactions which involve gaseous reagents, solid phase catalysts and relatively high temperatures and pressures.

The optimum overall catalyst combination for producing a desired product may not be the one that includes the optimum catalyst for Fischer-Tropsch synthesis and the optimum catalyst for olefin isomerization, since both steps may require totally different reaction conditions to be optimized. The overall optimum combination may be one that is the optimum for Fischer-Tropsch synthesis which defines a set of conditions, and then an olefin isomerization component that is optimized to work at the conditions needed for use with the Fischer-Tropsch catalyst. For example, the optimum conditions for Fischer-Tropsch synthesis may involve temperatures at a first temperature range, but the optimum olefin isomerization catalysts may operate best at temperatures at a different temperature range. When these "optimum" olefin isomerization catalysts are operated at temperatures in the first temperature range, they may be inefficient. Accordingly, it is preferred that the catalyst combinations include a combination that is optimum for both steps, Fischer-Tropsch synthesis and olefin isomerization, under the operating conditions imposed by the Fischer-Tropsch catalyst (satisfactory activity and relatively low methane yields). Alternatively, an optimum Fischer-Tropsch catalyst that operates satisfactorily under the optimum olefin isomerization conditions can be determined. Either way, it is important to test both catalyst components together, at least where both are to be combined in a single reactor using a single set of reaction conditions. However, leads for this screening of optimum catalyst combinations can come from searching the individual catalysts.

The properties of the reaction products generated during the evaluation of the libraries for a particular chemical reaction can be measured and correlated to specific combinations of catalysts. By screening numerous combinations of catalysts, the selection of the optimal combinations is more a function of the data collection method than the "rational" basis for selecting a useful catalyst combination. Optimum combinations can be rapidly determined by directly correlating the product streams obtained with the catalyst combinations within a particular array or sub-array.

Arrays

Libraries of catalysts can be prepared and evaluated using the devices and methods described herein. The first and second catalyst systems are preferably arranged (preferably in the reaction vessels) in the form of arrays. The catalysts can be, but need not be, mixed directly in the reaction vessels. Alternatively, they can be mixed ahead of time. In a less preferred embodiment, a single catalyst of a first type (a Fischer-Tropsch or olefin isomerization catalyst) is evaluated with a plurality of a second type of catalyst, and then subsequent catalysts of the first type can be evaluated with a plurality of the second type of catalyst, with the process repeated as desired. Preferably, the preparation of the catalyst libraries and/or the transfer of the catalysts to the reaction vessels is automated.

Preferably, the process involves generating a matrix including a first catalyst system and a second catalyst system. The synthesis is performed in a device which can handle the temperature and pressure requirements, as well as being able to handle a plurality of catalyst combinations (preferably more than 5 catalyst combinations at a time, more preferably greater than 20 catalyst combinations at a time, and, more preferably more than about 50 catalyst combinations at a time) and the product stream from the various reactions is then evaluated. Reaction vessels useful for conducting reactions under relatively high temperatures and pressures are well known to those of skill in the art.

The identity of the catalyst system in each reaction vessel or in each position in a reaction vessel can be stored in a computerized device, or identified via a bar code or other similar identifying means. The products of the reaction can be readily identified, for example, by gas chromatography (GC), a combination of gas chromatography and mass spectrometry (GC/MS), infrared heat emissions or infrared species analysis, or UV spectral analysis. To avoid contaminating the columns in chromatographic devices, it may be desirable to filter a representative sample of the product stream before it is placed on the column, for example using an in-line filter or an in-line solid phase extraction (SPE) column.

Reactors Suitable for Conducting Combinatorial Chemistry

Suitable reaction vessels for carrying out combinatorial chemistry include any suitable container that can hold a plurality of combinations of catalyst systems, which can contain from about 200 mg to about 100 g, preferably, from about 1 g to about 10 g of each catalyst combination, and that can handle the reaction conditions necessary for converting syngas to product streams including hydrocarbons in the distillate fuel and/or lube base oil ranges, for example conditions of increased pressure and temperature.

Any reaction vessel that is capable of being used to conduct a plurality of simultaneous reactions using gas phase reactants and solid catalysts under conditions of elevated temperature and pressure can be used. Such reaction vessels are well known to those of skill in the art. Examples of suitable devices include those described, for example, in U.S. Pat. No. 5,980,839 to Bier et al., U.S. Pat. No. 6,036,923 to Laugharn, Jr. et al., U.S. Pat. No. 6,030,917 to Weinberg et al., U.S. Pat. No. 6,001,311 to Brennan, the contents of each of which are hereby incorporated by reference.

The reaction vessel can contain multiple sample vessels, in parallel or in series, to perform combinatorial or sequential operations, respectively. The reactor can include a reaction region that includes a plurality of individual reaction cavities, each of which can have a port adapted to supply or remove reagents, solvents, gases and/or vacuum suction to the cavity. There can be a mixing region disposed adjacent to the reaction region, such that the reaction cavities open into the mixing region. The vessel can be constructed from a variety of materials, depending on the pressure and temperature requirements of the reaction, examples of which can include certain plastics, glass and certain metals such as stainless steel.

The scale of the synthetic reactions is preferably in the range of greater than about 200 mg, more preferably between one g and 100 g, although the scale can be modified depending on the amount of compound necessary for the particular application. Depending on the reaction vessel, it may be difficult to correlate the products obtained at smaller reaction scales with those obtained at commercial scale due to anticipated differences in heat transfer kinetics on scaleup. The reactions are typically performed under conditions of relatively high temperature and/or pressure. Following the reactions, the products can be characterized using a variety of means, for example, GC, GC/MS, HPLC and the like.

Robotic arms and multi-pipet devices can be used to add appropriate catalysts to the appropriate locations in the reaction vessel. When appropriate, the chemistry can be performed under varying conditions of temperature, pressure, flow rate and the like. When elevated temperatures and pressures are required, devices capable of handling elevated temperatures and pressures, particularly for use in combinatorial chemistry, are used.

In one embodiment, the reactions are carried out via computer control. The identity of each of the catalysts can be stored in a computer in a "memory map" or other means for correlating the data regarding the chemical reactions to the catalyst combinations in the reaction vessels. Alternatively, the chemistry can be performed manually and the information stored, for example on a computer.

Those of skill in the art can readily determine appropriate sets of reactions and reaction conditions to generate and/or evaluate the libraries of interest.

Analytical Chemistry

The products of the reactions can be analyzed in a high throughput manner, for example using HPLC, GC, GC/MS and/or other analytical methods. The products can be assayed for various properties, including octane and/or cetane values, degree of isomerization, olefin concentration, and the like.

Any device that can take samples from the individual positions in the reaction vessels and analyze the resulting compounds can be used. Preferably, the device is a chromatographic device, such as an analytical or preparative scale HPLC, GC or GC/MS, although other devices can be envisioned, depending on the chemistry performed. Since the product stream does not likely include UV-active compounds, the analytical equipment preferably includes an ELSD detector or other detector which is not dependent on UV absorption to detect a compound eluting from the column. Preferably, the analytical techniques are set up to handle a plurality of simultaneous analyses or otherwise optimized to handle the plurality of samples. After the chemical reactions take place, the contents of the reaction vessels (or a representative sample thereof) can be individually transferred to an analytical device. Those of skill in the art can readily optimize the reactions by varying various process conditions, for example reagent composition, temperature, pressure, flow rate and the like.

Particularly when iso-paraffin concentration is evaluated using the library, a combination of GC and MS is used. Isomers tend to have the same MS peaks, but elute at different times from the columns, and this technique allows rapid determination of the product stream.

Conditions are known in the art for determining the octane or cetane values based on known GC data, when a GC is performed on a representative sample of the product stream. These techniques may be particularly useful in evaluating the libraries for useful catalyst combinations for preparing products with desirable properties.

Database

Data regarding the catalyst combinations, reaction conditions and product streams can be stored in a relational database. The database can be used to find optimum catalyst combinations for a desired product stream, and can be particularly useful when the desired product stream varies depending on market factors. When the product requirements change, appropriate catalyst combinations and/or reaction conditions can be selected to prepare the desired product.

The device preferably includes a computer system capable of storing information regarding the identity of the catalysts and the product streams obtained, particularly when a plurality of different reaction conditions are used. Software for managing the data is stored on the computer. Relational database software can be used to correlate the identity of the ionic liquids, the reaction conditions (for example reagent composition, temperature and pressure) and the analytical data from each product stream. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the processes described herein. However, any software that is able to create a "memory map" of the catalysts in the reaction vessels and correlate that information with the information obtained from the chemical reactions can be used. This type of software is well known to those of skill in the art.

Combinatorial Optimization

The method steps involve:

a) preparing a logical array of a plurality of catalyst combinations in one or more reaction vessels, where the array includes one or more catalysts from a first catalyst system (Fischer-Tropsch catalysts in one embodiment, cobalt/ruthenium catalysts), and one or more catalysts from a second catalyst system (olefin isomerization catalysts), b) introducing syngas to the reaction vessel(s) under conditions which convert syngas to product streams, preferably including hydrocarbons in the distillate fuel and/or lube base oil ranges, c) analyzing the contents of the product streams, and e) optionally storing information regarding the identity of the catalysts and/or the contents of the product streams in a relational database.

It is preferred that the catalyst combinations (or composites) be evaluated in a single reactor, although the catalysts can be evaluated in separate reactors.

In order to compare catalyst combinations effectively, the reaction conditions (syngas composition, temperature and pressure) should be kept reasonably constant while evaluating the entire library. However, the reaction conditions can be varied in subsequent rungs to provide additional data. Accordingly, steps a–e can be repeated one or more times, with varying reaction conditions (for example, changes in syngas composition, temperatures and/or pressures) to obtain additional information.

The devices and processes described herein can be used for the rapid determination and optimization of desired catalyst activity for producing a given desired product stream. An array of catalysts systems can be screened and the optimum candidates for providing a desired product stream identified. This process can be repeated as desired to provide information regarding the catalyst systems of interest and the selection can be accelerated by the rapid modular synthesis of arrays for use in testing.

Combinations of catalysts which appear to provide desired product streams can optionally be scaled up (in a lead optimization step) to obtain additional data and to fine-tune the process. For example, once ideal catalyst combinations are identified in a lead generation step, the reaction conditions (syngas composition, temperature and pressure) and, optionally, catalyst pre-treatments, can be optimized in a lead optimization step.

The devices and processes described herein can be used for the logical and rapid analysis of synthetic results for various properties, including cetane and/or octane values, degree of isomerization, olefin concentration, and the like. One can determine the efficacy of a synthetic strategy by testing a series of loci within any given array. Accordingly, the general usefulness of various catalyst combinations for providing a desired product stream can be determined.

The devices and methods described herein provide for the complete control of the analysis of entire libraries of catalyst combinations.

The invention will be better understood with reference to the following non-limiting example.

EXAMPLE 1

Syngas Conversion Using Co/Ru and Olefin Isomerization Catalysts

A series of composite catalysts were evaluated in a Fischer-Tropsch synthesis model. The Fischer-Tropsch component of the catalysts was a cobalt/ruthenium on fluid alumina catalyst. It was evaluated alone and in combinations (50/50 by weight) of the catalyst and silica, alumina, a pillared clay and a variety of different zeolites and zeophosphates. Test conditions were chosen so that product distributions could be determined during short experiments of six to eight hours duration. These conditions favored lighter products than would likely be produced under optimal Fischer-Tropsch conditions. However, a reasonable correlation can be drawn between the results observed using these conditions and the results which would be obtained commercially. The products were analyzed on-stream using gas chromatography.

The pure Co/Ru catalyst and 50/50 composites of it with inert oxides such as silica produced about 10% methane, 6–8% ethane and propane, 50–55% $C_{4-11}$ and 25–35% $C_{12}+$ during 5–6 hours operation at 205° C. with a hydrogen/carbon monoxide ratio of about 1.5 and an inlet flow rate of 750 cc/g/h. The chain growth probability for $C_{5-10}$ chains was about 0.83 under those conditions. For more active composite catalysts, $C_{4-11}$ selectivity was as high as 83% and $C_{12}+$ selectivity as low as 1% under the same conditions. The chain growth probability for $C_{5-10}$ declined to about 0.60 in the presence of an acidic component, but chain growth probabilities (and thus, selectivities) for $C_{1-3}$ species were about the same as those for the Co/Ru catalyst itself.

A table listing the olefin isomerization catalysts, Bronsted acidity of the catalysts, and weight percent of the products ($C_{1-3}$, $C_{4-11}$ and $C_{12+}$ fractions) is shown below.

TABLE 1

| Catalyst | Bronsted Acidity | Wt. % $C_{1-3}$ | Wt. % $C_{4-11}$ | Wt. % $C_{12+}$ |
|---|---|---|---|---|
| ZSM-5 | S1 (195) | 11.3 | 83.4 | 5.4 |
| SSZ-25 | S1 (210) | 11.7 | 81.9 | 6.4 |
| Beta | S1 (130) | 16.3 | 81.2 | 2.5 |
| SSZ-42 | VS (110) | 13.0 | 80.3 | 6.7 |
| ZSM-23 | S1 (120) | 12.8 | 79.9 | 7.3 |
| Al-SSZ-33 | S1 (75) | 20.8 | 78.3 | 0.9 |
| CBV-760 | S1 (150) | 14.8 | 78.2 | 6.9 |
| SSZ-26 | S1 (90) | 15.1 | 77.4 | 7.5 |
| ZSM-48 | S1 (40) | 20.0 | 73.7 | 6.4 |
| MOR | S1 (450) | 23.2 | 72.6 | 4.2 |
| EU-1 | S1 (60) | 20.1 | 72.0 | 7.8 |
| ZSM-11 | S1 (200) | 22.1 | 71.8 | 6.1 |
| SSZ-32 | S1 (145) | 16.4 | 71.7 | 11.9 |
| SAPO-Y | (125) | 20.4 | 71.5 | 8.2 |
| β-SSZ-33 | W (6) | 12.1 | 71.0 | 16.9 |
| Gmelinite | M (16) | 23.7 | 70.3 | 6.0 |
| FER | S1 (240) | 18.4 | 69.5 | 12.1 |
| SSZ-35 | S1 (80–110) | 24.7 | 68.6 | 6.7 |
| SUZ-4 | S1 (210) | 13.8 | 68.4 | 17.8 |
| SSZ-41 | VS (23) | 27.7 | 67.0 | 5.3 |
| CBV-712 | VS, S1 (470) | 28.2 | 66.6 | 5.3 |
| SAPO-40 | VS (20) | 16.5 | 66.2 | 17.3 |
| NU-87 | (180) | 31.5 | 65.9 | 2.6 |
| ZSM-57 | W (98) | 15.7 | 63.0 | 21.3 |
| CBV-500T | S1 (720) | 14.0 | 62.8 | 23.2 |
| RE-ACHM | (38) | 21.7 | 61.7 | 11.2 |
| ZSM-57 | W (98) | 16.0 | 61.6 | 22.4 |
| SAPO-41 | VS (20), S3 (125) | 32.6 | 59.4 | 8.0 |
| MAPSO-31 | (35) | 17.0 | 58.2 | 24.8 |
| SSZ-41 | V2 (23) | 11.1 | 58.1 | 30.9 |
| CBV-790 | S1 (71) | 14.4 | 56.4 | 29.2 |
| Offretite | S1 (250) | 18.3 | 55.2 | 26.5 |
| $Al_2O_3$ | none | 11.9 | 53.6 | 34.5 |
| No additive | none | 18.6 | 52.0 | 29.4 |
| $SiO_2$ | none | 17.5 | 49.6 | 33.0 |

While not wishing to bound to a particular theory, it is believed that the acidic components alter the Fischer-Tropsch product distribution by converting alpha-olefin intermediates to iso-olefins and/or internal olefins. Alpha-olefins, particularly low molecular weight ($C_{2-6}$) alpha-olefins, take part in hydrocarbon chain growth by initiating new chains. This causes the $C_2$+ chain growth probability to be higher than if they did not take part in new chain growth. Due to steric hindrance at the active sites, internal olefins and iso-olefins are much less likely to incorporate into the Fischer-Tropsch synthesis, thus lowering the chain growth probability for $C_4$+ chains. There is no effect on $C_{2-3}$ chains, since these only have one olefin isomer.

The composite catalysts described herein permit the Fischer-Tropsch synthesis to operate with relatively high chain growth probabilities through about $C_3$, and with relatively low chain growth probabilities above $C_4$. The reaction therefore has relatively low methane and wax formation, and forms a product stream that mainly includes hydrocarbons in the $C_{5-20}$ range.

When the acidities of USY zeolites were too low (for example, SAR above about 70), very little olefin isomerization was observed. However, when the USY's were very acidic (for example, SAR below about 5), rapid deactivation was observed. Accordingly, using catalysts with intermediate acidity can be preferred. As shown in FIG. 1, when the SAR was between about 30 and 60, optimum syngas conversions were obtained. When the SAR was 90 or greater or 12 or less, less than optimum syngas conversions were obtained.

Those skilled in the art will recognize, or be able to ascertain using no more than routine experimentation, many equivalents to the specific embodiments of the invention described herein. Such equivalents are intended to be encompassed by the following claims.

I claim:

1. A method for optimizing the conversion of syngas to higher molecular weight products via Fischer-Tropsch synthesis, comprising:
    a) preparing a first library of cobalt/ruthenium Fischer-Tropsch catalysts
    b) preparing a second library of olefin isomerization catalysts
    c) reacting syngas with a plurality of combinations of catalysts from the first and second libraries under appropriate reaction conditions to form a plurality of reaction products.

2. The method of claim 1, further comprising analyzing the reaction products.

3. The method of claim 1, further comprising storing information regarding the identity of the catalysts in the plurality of combinations of catalysts in a database.

4. The method of claim 2, further comprising storing information regarding the analysis of the reaction products in a database.

5. The method of claim 1, wherein the combinations of catalysts are arranged in a logical array.

6. The method of claim 1, wherein step d) is repeated at least one time using different reaction conditions.

7. The process of claim 6, wherein the reaction conditions which are varied are selected from the group consisting of temperature, pressure, syngas composition, and flow rate.

8. The method of claim 1, wherein at least one of the catalysts is a zeolite.

9. The method of claim 8, wherein at least one of the catalysts is an intermediate pore size zeolite.

10. The method of claim 1, wherein the reaction product includes iso-paraffins in the jet fuel range.

11. The method of claim 1, wherein the reaction product includes iso-paraffins in the diesel fuel range.

12. The method of claim 1, wherein the reaction product includes iso-paraffins in the lube base oil range.

13. A method for rapidly determining an appropriate set of reaction conditions and catalyst combinations to form a desired product via conversion of syngas to hydrocarbons comprising:
    a) preparing a first library of cobalt/ruthenium Fischer-Tropsch catalysts,
    b) preparing a second library of olefin isomerization catalysts,
    c) preparing a plurality of combinations of catalysts from the first and second libraries in a logical manner, and
    d) reacting syngas with the catalysts under a plurality of reaction conditions to form a plurality of reaction products, wherein each set of reaction conditions is applied to all or substantially all of the catalyst combinations,
    e) storing information regarding the products of the reactions in a database, and
    f) identifying an appropriate set of reaction conditions and catalyst combinations to produce the desired product.

14. A method for rapidly determining an appropriate set of reaction conditions and catalysts to form a desired product comprising:
   a) preparing a library of cobalt/ruthenium catalysts that are active at both Fischer-Tropsch synthesis and olefin isomerization,
   b) reacting syngas with the catalysts under a plurality of reaction conditions to form a plurality of reaction products, wherein each set of reaction conditions is applied to all or substantially all of the catalysts,
   c) storing information regarding the products of the reactions in a database, and
   d) identifying an appropriate set of reaction conditions and catalysts to produce the desired product.

* * * * *